United States Patent [19]

John et al.

[11] 4,405,804

[45] Sep. 20, 1983

[54] METHOD FOR PREPARING 2-CHLOROETHYLSILANES

[75] Inventors: Peter John; Reinhold Artes; Volker Frey, all of Burghausen; Matthias Scherer, Emmerting, all of Fed. Rep. of Germany

[73] Assignee: Wacker-Chemie GmbH, Munich, Fed. Rep. of Germany

[21] Appl. No.: 414,161

[22] Filed: Sep. 2, 1982

[30] Foreign Application Priority Data

Nov. 5, 1981 [DE] Fed. Rep. of Germany ....... 3144020

[51] Int. Cl.$^3$ ............................................... C07F 7/08
[52] U.S. Cl. ................................................... 556/476
[58] Field of Search ........................................ 556/476

[56] References Cited

U.S. PATENT DOCUMENTS

| | | | |
|---|---|---|---|
| 3,801,614 | 4/1974 | Lohmann et al. | 556/476 |
| 3,933,881 | 1/1976 | Föry et al. | 556/476 |
| 4,049,690 | 9/1977 | Seiler et al. | 556/476 |
| 4,055,584 | 10/1977 | Kny | 556/476 |

FOREIGN PATENT DOCUMENTS

2458962  6/1975  Fed. Rep. of Germany ...... 556/476

*Primary Examiner*—Paul F. Shaver

[57] ABSTRACT

A method for preparing 2-chloroethylsilanes which comprises reacting a vinylchlorosilane with hydrogen chloride in the presence of a catalyst consisting of at least one organoaluminum compound, or the product obtained from the in situ reaction of such an aluminum compound with at least one of the reactants. The catalyst may first be deactivated, if desired, by the addition of a liquid organopolysiloxane to the reaction mixture, prior to the distillation of the 2-chloroethylsilane.

5 Claims, No Drawings

METHOD FOR PREPARING 2-CHLOROETHYLSILANES

The present invention relates to a method for preparing chloroalkylsilanes and more particularly to a method for preparing 2-chloroethylsilanes.

BACKGROUND OF THE INVENTION

It is known that chloroalkylsilanes, especially 2-chloroethylsilanes, also known as beta-chloroethylsilane, can be prepared by reacting vinylchlorosilanes with hydrogen chloride in the presence of a catalyst. Such a method is described, for example, in U.S. Pat. No. 4,049,690 to Seiler et al, in which a vinyltrichlorosilane is reacted with hydrogen chloride at a temperature of from 30° to 65° C. and at a pressure of from 740–790 mm Hg in the presence of from 1.0 to 15 percent by weight based on the weight of the vinyltrichlorosilane of a Lewis acid catalyst.

Compared to methods known heretofore, the method of the present invention has certain advantages. For example, smaller amounts of catalyst are required and essentially quantitative yields are obtained. Moreover, the method may be performed at pressures below atmospheric pressure so that it is no longer necessary to provide for the removal of excess hydrogen chloride. Furthermore, it is considerably easier to obtain 2-chloroethylsilane free of impurities.

Therefore, it is an object of the present invention to provide a method for preparing chloroalkylsilanes. Another object of the present invention is to provide a method for preparing 2-chloroethylsilane. Still another object of this invention is to provide a method for preparing 2-chloroethylsilane in essentially quantitative yields. A further object of the present invention is to provide a method for preparing essentially pure 2-chloroethylsilane.

SUMMARY OF THE INVENTION

The foregoing objects and others which will become apparent from the following description are accomplished, generally speaking, by providing a method for preparing 2-chloroethylsilane which comprises reacting vinylchlorosilane with hydrogen chloride in the presence of a catalytic amount of an organoaluminum compound or the product obtained from the in situ reaction of the organoaluminum compound with one of the reactants. The catalyst may be deactivated, if desired, prior to distilling off the 2-chloroethylsilane.

DETAILED DESCRIPTION OF THE INVENTION

The vinylchlorosilanes used in the process of this invention are preferably those having the general formula:

$$(CH_2=CH)_a Si(CH_3)_b Cl_{4-a-b},$$

where a is 1 or 2 and b is 0 or 1, with the proviso that when a is 2, b must be 0.

Suitable examples of silanes are vinyltrichlorosilane, vinylmethyldichlorosilane and divinyldichlorosilane.

Hydrogen chloride is preferably used in an amount of from about 1 to 1.1 gram molecule per gram molecule of vinyl group present on the vinylchlorosilane.

The organoaluminum compounds used in the process of this invention are preferably those having the general formula $$R_c AlY_{3-c}$$

where R represents the same or different alkyl radicals having from 1 to 4 carbon atoms, Y is halogen or hydrogen and c is 1, 2 or 3.

Examples of suitable hydrocarbon radicals represented by R are alkyl radicals such as the methyl, ethyl, n-propyl, isopropyl, n-butyl, sec-butyl and the tert-butyl radical, and alkenyl radicals such as the vinyl, allyl, methallyl and isopropenyl radical.

It is preferred that Y be a halogen, especially chlorine; however, Y may also be fluorine, bromine or iodine.

Individual examples of organoaluminum compounds which may be used in the process of this invention are the following:
ethyl aluminum sesquichloride
diethyl aluminum chloride
ethyl aluminum dichloride
trimethylaluminum
methyl aluminum sesquichloride
triethylaluminum
tri-n-propylaluminum
n-propyl aluminum dichloride
di-n-butyl aluminum hydride Preferably the organoaluminum compounds are liquid at room temperature and have a boiling point above about 150° at 1 bar (abs.). Because of its availability, ethyl aluminum sesquichloride is the preferred organoaluminum compound. Mixtures consisting of various organoaluminum compounds may also be used.

The term "organoaluminum compound" also includes the product obtained from the in situ reaction of the organoaluminum compound with one of the reactants.

It is preferred that the organoaluminum compound be employed in an amount of from 0.05 to 1 percent by weight, based on the weight of the vinylchlorosilane used.

The process of this invention is preferably carried out at temperatures between about −10° C. and +55° C., but preferably not in excess of about 50° C., and at 0.1 bar (abs.) to 15 bar (abs.), with the preferred pressured being between about 0.1 bar (abs.) and normal atmospheric pressure.

It is preferred that water be excluded as far as possible.

The process of this invention is preferably carried out in stages; however, it may be performed as a semi-continuous process or as a continuous process. If the process of this invention is performed as a semi-continuous process or as a continuous process, then it may take place in a helicoidal pipe or a U-shaped or annular pipe. In such a pipe the reactor's contents can be recycled at a rate of at least 1000 cm/minute.

It is preferred that the catalyst be deactivated before the desired product is removed by distillation. Deactivation is preferably achieved by adding an organopolysiloxane which is liquid at room temperature, for example, a trimethylsiloxy endblocked dimethylpolysiloxane or an organopolysiloxane having an Si-bonded hydroxyl group in each of its terminal units, or a cyclic organopolysiloxane such as an octamethylcyclotetrasiloxane, to the mixture from which the 2-chloroethylsilane is to be recovered by distillation. However, deactivation can also be achieved by adding by alkali metal chloride such as sodium chloride or ammonium chloride to the mixture from which 2-chloroethylsilane is to be recovered. Mixtures of two or more different agents may be used to deactivate the catalyst.

When the catalyst is deactivated with the aid of an organopolysiloxane, the organopolysiloxane is preferably used in an amount of from 1 to 1.5 gram atoms of Si-bonded oxygen for each mole of the organoaluminum compound used.

The 2-halogenethylsilanes may be used as an intermediate in the manufacture of plant growth regulators.

EXAMPLE 1

(a) The pressure in a 4-liter three-necked flask equipped with an agitator, a reflux condenser, a thermometer and a gas supply conduit, is lowered first to 16 mbar (abs.) and then raised with nitrogen to the pressure of the surrounding atmosphere, i.e., approximately 1000 mbar (abs.). After repeating this step 5 times, about 2.6 liters (20.4 mols) of vinyltrichlorosilane and 7.5 ml (0.25 percent by weight based on the weight of the vinyltrichlorosilane) of ethyl aluminum sesquichloride are placed in the flask under a stream of nitrogen. About 767 g (21 mols) of hydrogen chloride are added to the mixture over a period of 8 hours. External cooling is used to ensure that the contents of the flask do not exceed about 50° C. About 4010 g of crude product is obtained. Gas chromatographic analysis shows that the product contains 99 percent by weight of 2-chloroethyltrichlorosilane, which is about 99.3 percent of theory.

(b) About 2005 g of the crude product prepared in Example 1(a) above, are mixed with 5 ml of a trimethylsiloxy end-blocked dimethylpolysiloxane which has a viscosity of about 5 mm$^2$.s$^{-1}$ at 25° C. The mixture is then stirred for 15 minutes and then distilled at 70° C. and at 67 mbar (abs.). About 1960 g of 2-chloroethyltrichlorosilane is recovered which has a purity of 99.5 percent by weight as determined by gas chromatography.

(c) The remaining 2005 g of crude product prepared in accordance with Example 1(a) above, are distilled at 70° C. and at 67 mbar (abs.). About 1810 g of 2-chloroethyltrichlorosilane are recovered which has a purity of 96 percent by weight, as determined by gas chromatography. The residual 4 percent by weight, consisted primarily of vinyltrichlorosilane, which formed during the distillation of the 2-ethyltrichlorosilane.

EXAMPLE 2

The pressure inside a 500 ml three-necked flask equipped with an agitator, a reflux condenser, a thermometer and a gas conduit, is lowered first to 16 mbar (abs.) and then raised with the aid of nitrogen to the pressure of the surrounding atmosphere. After repeating this step 5 times, about 255 ml (2 mols) of vinyltrichlorosilane and 2 ml (0.66 percent by weight based on the weight of the vinyltrichlorosilane) of ethyl aluminum sesquichloride are added to the flask under a flow of nitrogen and thereafter hydrogen chloride is added. The rapid reaction of the hydrogen chloride caused the pressure inside the flask to decrease below 1000 mbar (abs.). Whenever the pressure within the flask exceeded about 1000 mbar (abs.) due to an excess of hydrogen chloride, the supply of hydrogen chloride is curtailed until the pressure subsided to less than 1000 mbar (abs.). During this procedure, external cooling is employed to ensure that the contents of the flask did not exceed 40° C. About 98 percent by weight of the vinyltrichlorosilane is converted into 2-chloroethyltrichlorosilane.

EXAMPLE 3

The 4-liter three-necked flask described in Example 1 is rinsed several times with nitrogen and then 1.83 kg (12 mols) of divinyldichlorosilane and 14 ml (0.84 percent by weight, based on the weight of the divinyldichlorosilane) of ethyl aluminum sesquichloride are added to the flask under a blanket of nitrogen. About 870 g (24 mols) of hydrogen chloride are then added to the mixture over a period of about 4 hours. External cooling is employed to ensure that the contents of the flask remain between −6° and 0° C. About 2.6 kg of crude product is recovered which is analyzed by gas chromatography. The product has the following composition:

81 percent by weight of bis-(2-chloroethyl)-dichlorosilane 4 percent by weight of 2-chloroethyltrichlorosilane 4 percent by weight of 2-chloroethylvinyldichlorosilane 5 percent by weight of vinyltrichlorosilane 6 percent by weight of unidentified constituents

EXAMPLE 4

The 4-liter three-necked flask of Example 1 is rinsed several times with nitrogen in accordance with the procedure of Example 1(a). Then about 1.91 kg (13.5 mols) of vinylmethyldichlorosilane and 10 ml (0.58 percent by weight based on the weight of the vinylmethyldichlorosilane) of ethyl aluminum sesquichloride are added to the flask under a blanket of nitrogen. About 493 g (13.5 mols) of hydrogen chloride are then added to the mixture within about 5.5 hours. External cooling is used to ensure that the contents of the flask remained between −2° C. and 0° C. About 2.35 kg of crude product is obtained having the following composition, as determined by gas chromatography:

92 percent by weight of (2-chloroethyl)-methyldichlorosilane 2 percent by weight of vinylmethyldichlorosilane 5 percent by weight of methyltrichlorosilane 1 percent by weight of unidentified constituents The crude product is then mixed with 10 ml of a trimethylsiloxy terminated polydimethylsiloxane having a viscosity of about 5 mm$^2$.s$^{-1}$ at 25° C. The product is distilled at 52° C. and at 20 mbar (abs.). About 2.05 kg of (2-chloroethyl)-methyldichlorosilane is recovered which has a purity of 99 percent by weight, as determined by gas chromatography. A yield of about 86 percent, based on theoretical is obtained.

What is claimed is:

1. A method for preparing 2-chloroethylsilanes which comprises reacting a vinylchlorosilane with hydrogen chloride in the presence of a catalyst selected from the group consisting of an organoaluminum compound, and the product obtained from the in situ reaction of the organoaluminum compound with at least one of the reactants.

2. The method of claim 1, wherein the catalyst is deactivated prior to removing the 2-chloroethylsilane.

3. The method of claim 1, wherein the organoaluminum compound is an organoaluminum compound having the general formula $$R_c AlY_{3-c}$$

where R is an alkyl radical having from 1 to 4 carbon atoms, Y is selected from the group consisting of halogen, and hydrogen and c is 1, 2 or 3.

4. The method of claims 1, 2 or 3, wherein the organoaluminum compound is used in an amount of from 0.05 to 1 percent by weight, based on the weight of the vinylchlorosilane.

5. The method of claims 1, 2 or 3, wherein the catalyst is deactivated by adding an organopolysiloxane which is liquid at room temperature, to the mixture and thereafter distilling off the 2-chloroethylsilane.

* * * * *